US00PP16019P2

(12) United States Plant Patent
Repp

(10) Patent No.: US PP16,019 P2
(45) Date of Patent: Oct. 4, 2005

(54) ***COLEUS* PLANT NAMED 'SUNDANCER6'**

(50) Latin Name: *Solenostemon scutellarioides*
Varietal Denomination: Sundancer6

(76) Inventor: Ralph J. Repp, 160 Gator Dr., Waynesville, NC (US) 28785

( * ) Notice: Subject to any disclaimer, the term of this patent is extended or adjusted under 35 U.S.C. 154(b) by 25 days.

(21) Appl. No.: 10/862,860

(22) Filed: Jun. 7, 2004

(51) Int. Cl.[7] ..... A01H 5/00

(52) U.S. Cl. ..... Plt./373
(58) Field of Search ..... Plt./373

*Primary Examiner*—Kent Bell
(74) *Attorney, Agent, or Firm*—C. A. Whealy

(57) ABSTRACT

A new and distinct cultivar of *Coleus* plant named 'Sundancer6', characterized by its large, upright and mounded plant habit; vigorous and freely branching growth habit; yellow green-colored lateral branches and leaf petioles; elliptic to rhomboidal-shaped leaves with irregular lobation; and purple-colored leaves with dark purple to warmish brown-colored margins.

1 Drawing Sheet

Botanical classification/cultivar designation: *Solenostemon scutellarioides* cultivar Sundancer6.

BACKGROUND OF THE INVENTION

The present Invention relates to a new and distinct cultivar of *Coleus* plant, botanically known as *Solenostemon scutellarioides*, and hereinafter referred to by the cultivar name 'Sundancer6'.

The new cultivar was discovered by the Inventor in a controlled environment in Waynesville, N.C. as a chemically-induced mutation of the *Solenostemon scutellarioides* cultivar Grace Ann, not patented. Plants of the cultivar Grace Ann were treated with colchicine to induce mutations. The new *Coleus* was observed within a population of chemically-treated plants of the parent cultivar in October, 2001. This seedling was selected on the basis of its unique leaf coloration.

Asexual reproduction of the new cultivar by terminal cuttings in Waynesville, N.C., has shown that the unique features of this new *Coleus* are stable and reproduced true to type in successive generations.

SUMMARY OF THE INVENTION

Plants of the cultivar Sundancer6 have not been observed under all possible environmental conditions. The phenotype may vary somewhat with variations in environment such as temperature and light intensity without, however, any variance in genotype.

The following traits have been repeatedly observed and are determined to be the unique characteristics of 'Sundancer6'. These characteristics in combination distinguish 'Sundancer6' as a new and distinct cultivar:

1. Large, upright and mounded plant habit.
2. Vigorous and freely branching growth habit.
3. Yellow green-colored lateral branches and leaf petioles.
4. Elliptic to rhomboidal-shaped leaves with irregular lobation.
5. Purple-colored leaves with dark purple to warmish brown-colored margins.

Plants of the new *Coleus* are most similar to plants of the parent, the cultivar Grace Ann. In side-by-side comparisons conducted in Waynesville, N.C., plants of the new *Coleus* differed from plants of the cultivar Grace Ann in the following characteristics:

1. Plants of the new *Coleus* were larger than plants of the cultivar Grace Ann.
2. Plants of the new *Coleus* had narrower leaves than plants of the cultivar Grace Ann.
3. Plants of the new *Coleus* and the cultivar Grace Ann differed in leaf coloration as plants of the cultivar Grace Ann had violet pink and green bi-colored leaves.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Coleus*.

The photograph at the top of the sheet comprises a side perspective view of typical plant of 'Sundancer6' grown in a container.

The photograph at the bottom of the sheet comprises a close-up view of typical leaves of 'Sundancer6'.

DETAILED BOTANICAL DESCRIPTION

The cultivar Sundancer6 has not been observed under all possible environmental conditions. The phenotype may vary somewhat with variations in environment such as temperature and light intensity without, however, any variance in genotype.

The aforementioned photographs, following observations and measurements describe plants grown during the winter and spring in Encinitas, Calif., in a polyethylene-covered greenhouse and under conditions which approximate commercial production cultural and environmental conditions. Plants were about 12 weeks from rooted cuttings and were grown three plants per one-gallon containers. During the production of the plants, day temperatures averaged 24° C., night temperatures averaged 19° C. and light levels ranged from 2,500 to 5,000 footcandles.

In the following description, color references are made to The Royal Horticultural Society Colour Chart, 1995 Edition, except where general terms of ordinary dictionary significance are used.

Botanical classification: *Solenostemon scutellarioides* cultivar Sundancer6.

Parentage: Chemically-induced mutation of the *Solenostemon scutellarioides* cultivar Grace Ann, not patented.

Propagation:

*Type cutting*.—Terminal cuttings.

*Time to initiate roots*.—Summer: About 7 days at 20° C. Winter: About 9 days at 20° C.

*Time to develop roots*.—Summer: About 18 days at 20° C. Winter: About 20 days at 20° C.

*Root description*.—Fine; white in color.

*Rooting habit*.—Freely branching, dense.

Plant description:

*Form*.—Large, upright and mounded plant habit. Vigorous growth habit.

*Plant height*.—About 42 cm.

*Plant diameter, single plant*.—About 25 cm.

*Branching habit*.—Freely branching with about four to five lateral branches per plant.

*Lateral branches*.—Length: About 34 cm. Diameter: About 8 mm. Internode length: About 4.5 to 5 cm. Shape, in cross-section: Squarish. Texture: Slightly pubescent. Color: 145C.

*Foliage description*.—Arrangement: Opposite; simple. Length: About 13 cm. Width: About 6.4 cm. Shape: Elliptic to rhomboidal. Apex: Acuminate. Base: Attenuate. Margin: Irregularly lobed. Texture, upper and lower surfaces: Slightly pubescent. Venation pattern: Pinnate, arcuate. Color: Developing foliage, upper surface: Center, 53B; towards margins, 183A to 183B. Young foliage, lower surface: 185B. Fully expanded foliage, upper surface: Center, 53B to 185C; towards margins, warmer brown than but closest to 200B to 200C. Fully expanded foliage, lower surface: 184B. Venation, upper surface: 185C. Venation, lower surface: 145D. Petiole length: About 5 cm. Petiole diameter: About 2.5 mm. Petiole color: 144B.

Flower description: Flower development has not been observed.

Disease/pest resistance: Plants of the new *Coleus* have not been noted to be resistant to pathogens or pests common to *Coleus*.

Temperature tolerance: Plants of the new *Coleus* have been observed to tolerate temperatures from 4 to 32° C.

It is claimed:

1. A new and distinct cultivar of *Coleus* plant named 'Sundancer6', as illustrated and described.

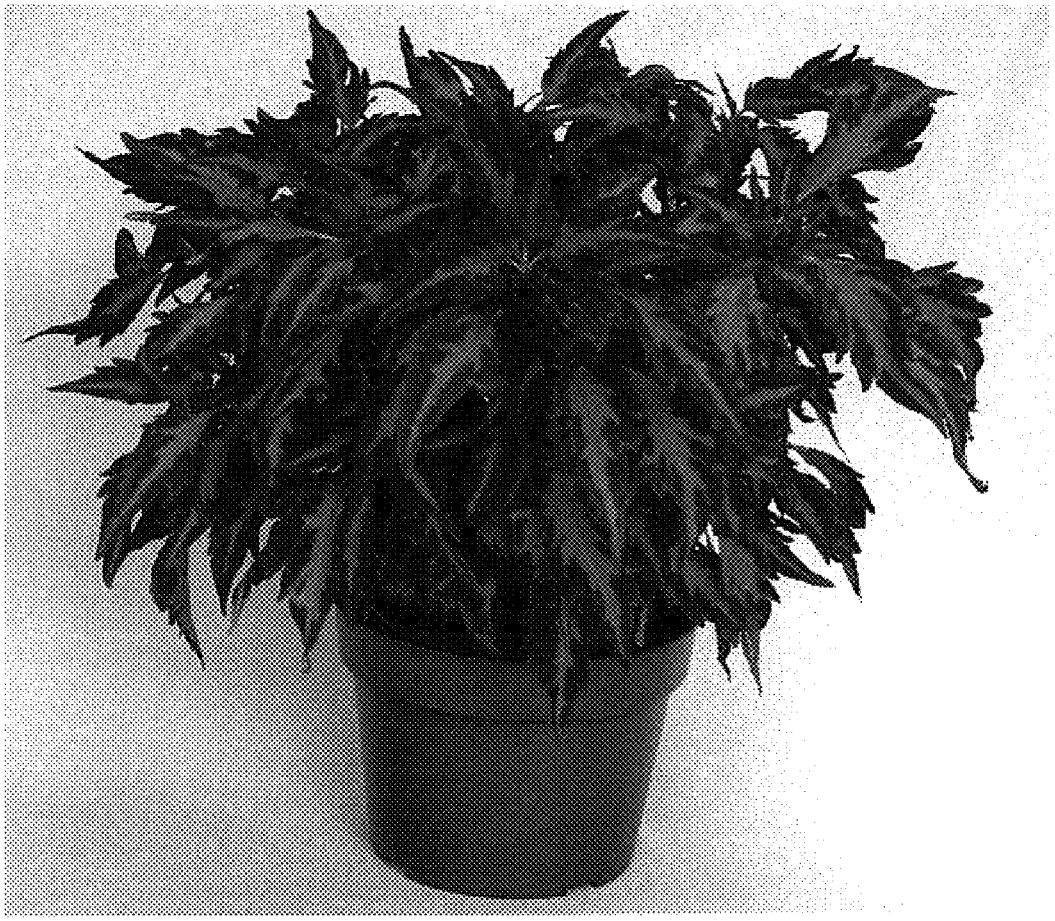
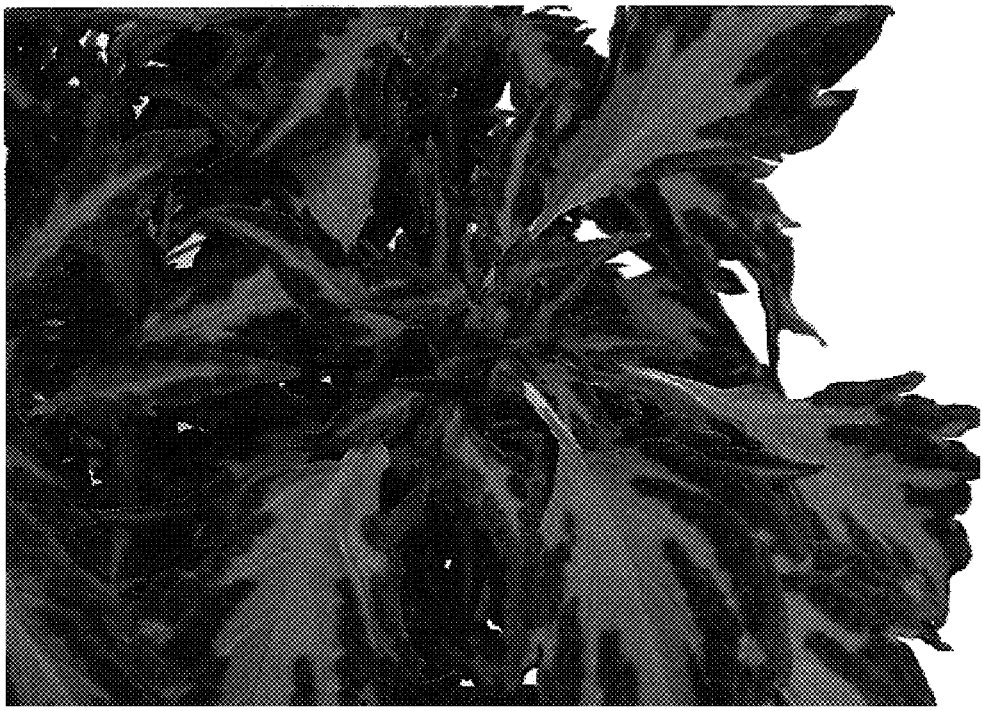

* * * * *